US008728130B2

(12) United States Patent
Kirschman (10) Patent No.: US 8,728,130 B2
(45) Date of Patent: May 20, 2014

(54) IMPLANT PLATE SCREW LOCKING SYSTEM AND SCREW HAVING A LOCKING MEMBER

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 198 days.

(21) Appl. No.: 13/155,726

(22) Filed: Jun. 8, 2011

(65) Prior Publication Data
US 2011/0238123 A1  Sep. 29, 2011

Related U.S. Application Data

(63) Continuation of application No. 11/778,284, filed on Jul. 16, 2007, now Pat. No. 7,963,982.

(51) Int. Cl.
A61B 17/80 (2006.01)
A61B 17/84 (2006.01)

(52) U.S. Cl.
USPC .......................................................... 606/291

(58) Field of Classification Search
USPC .......... 411/114, 125, 127, 186, 326; 606/289, 606/291, 294
See application file for complete search history.

(56) References Cited

U.S. PATENT DOCUMENTS

| | | | |
|---|---|---|---|
| 1,025,008 A | 4/1912 | Miner | |
| 2,677,369 A | 5/1954 | Knowles | |
| 3,848,601 A | 11/1974 | Ma et al. | |
| 3,867,728 A | 2/1975 | Stubstad et al. | |
| 4,157,715 A | 6/1979 | Westerhoff | |
| 4,309,777 A | 1/1982 | Patil | |
| 4,349,921 A | 9/1982 | Kuntz | |
| 4,488,543 A | 12/1984 | Tornier | |
| 4,553,273 A | 11/1985 | Wu | |
| 4,599,086 A | 7/1986 | Doty | |
| 4,611,581 A | 9/1986 | Steffee | |
| 4,696,290 A | 9/1987 | Steffee | |
| 4,714,469 A | 12/1987 | Kenna | |
| 4,743,256 A | 5/1988 | Brantigan | |
| 4,759,766 A | 7/1988 | Buettner-Janz et al. | |
| 4,763,456 A * | 8/1988 | Giannuzzi ........................ 52/410 |
| 4,834,757 A | 5/1989 | Brantigan | |
| 4,878,915 A | 11/1989 | Brantigan | |
| 4,988,349 A | 1/1991 | Pennig | |
| 4,997,432 A | 3/1991 | Keller | |
| 5,041,113 A | 8/1991 | Biedermann et al. | |
| 5,084,049 A | 1/1992 | Asher et al. | |
| 5,085,660 A | 2/1992 | Lin | |
| 5,192,327 A | 3/1993 | Brantigan | |
| 5,246,443 A | 9/1993 | Mai | |
| 5,261,911 A | 11/1993 | Carl | |

(Continued)

FOREIGN PATENT DOCUMENTS

CA 1292596 12/1991
CA 2133276 4/1995

(Continued)

Primary Examiner — Christian Sevilla
(74) Attorney, Agent, or Firm — Jacox, Meckstroth & Jenkins (57) ABSTRACT

Spinal fusion system and method utilizing an implant and screw, wherein at least one pawl is mounted on or integral with the screw to prevent said plate or screw from moving in at least one of an axial direction or a rotational direction.

17 Claims, 7 Drawing Sheets

(56) References Cited

U.S. PATENT DOCUMENTS

| | | | |
|---|---|---|---|
| 5,267,423 A | 12/1993 | Giannuzzi | |
| 5,275,601 A | 1/1994 | Gogolewski et al. | |
| 5,290,312 A | 3/1994 | Kojimoto et al. | |
| 5,324,290 A | 6/1994 | Zdeblick et al. | |
| 5,330,473 A | 7/1994 | Howland | |
| 5,364,399 A | 11/1994 | Lowery et al. | |
| 5,405,391 A | 4/1995 | Hednerson et al. | |
| 5,425,772 A | 6/1995 | Brantigan | |
| 5,439,463 A | 8/1995 | Lin | |
| 5,549,612 A | 8/1996 | Yapp et al. | |
| 5,554,191 A | 9/1996 | Lahille et al. | |
| 5,601,551 A | 2/1997 | Taylor et al. | |
| 5,601,553 A | 2/1997 | Trebing et al. | |
| 5,616,142 A | 4/1997 | Yuan et al. | |
| 5,616,144 A | 4/1997 | Yapp et al. | |
| 5,620,443 A | 4/1997 | Gertzbein et al. | |
| 5,672,177 A | 9/1997 | Seldin | |
| 5,681,310 A | 10/1997 | Yuan et al. | |
| 5,681,311 A | 10/1997 | Foley et al. | |
| 5,702,395 A | 12/1997 | Hopf | |
| 5,713,899 A | 2/1998 | Marnay et al. | |
| 5,713,900 A | 2/1998 | Benzel et al. | |
| 5,716,415 A | 2/1998 | Steffee | |
| 5,720,746 A | 2/1998 | Soubeiran | |
| 5,776,196 A | 7/1998 | Matsuzaki et al. | |
| 5,843,082 A | 12/1998 | Yuan et al. | |
| 5,876,402 A | 3/1999 | Errico et al. | |
| 5,888,228 A | 3/1999 | Knothe et al. | |
| 5,904,683 A | 5/1999 | Pohndorf et al. | |
| 5,925,047 A | 7/1999 | Errico et al. | |
| 5,951,558 A | 9/1999 | Fiz | |
| 5,954,722 A | 9/1999 | Bono | |
| 6,030,389 A | 2/2000 | Wagner et al. | |
| 6,066,175 A | 5/2000 | Henderson et al. | |
| 6,106,557 A | 8/2000 | Robioneck et al. | |
| 6,136,002 A | 10/2000 | Shih et al. | |
| 6,139,550 A | 10/2000 | Michelson | |
| 6,152,927 A | 11/2000 | Farris et al. | |
| 6,159,211 A | 12/2000 | Boriani et al. | |
| 6,159,213 A | 12/2000 | Rogozinski | |
| 6,159,245 A | 12/2000 | Meriwether et al. | |
| 6,171,307 B1 | 1/2001 | Orlich | |
| 6,193,721 B1 | 2/2001 | Michelson | |
| D440,311 S | 4/2001 | Michelson | |
| 6,224,602 B1 | 5/2001 | Hayes | |
| 6,235,033 B1 | 5/2001 | Brace et al. | |
| 6,235,034 B1 | 5/2001 | Bray | |
| 6,235,059 B1 | 5/2001 | Benezech et al. | |
| 6,245,108 B1 | 6/2001 | Biscup | |
| 6,258,089 B1 | 7/2001 | Campbell et al. | |
| 6,261,291 B1 | 7/2001 | Talaber et al. | |
| 6,261,586 B1 | 7/2001 | McKay | |
| 6,264,655 B1 | 7/2001 | Pisharodi | |
| 6,293,949 B1 | 9/2001 | Justis et al. | |
| D449,692 S | 10/2001 | Michelson | |
| 6,306,136 B1 | 10/2001 | Baccelli | |
| 6,306,139 B1 | 10/2001 | Fuentes | |
| 6,328,738 B1 | 12/2001 | Suddaby | |
| 6,361,537 B1 | 3/2002 | Anderson | |
| 6,368,351 B1 | 4/2002 | Glenn et al. | |
| 6,383,186 B1 | 5/2002 | Michelson | |
| 6,398,783 B1 | 6/2002 | Michelson | |
| 6,413,259 B1 | 7/2002 | Lyons et al. | |
| 6,416,528 B1 | 7/2002 | Michelson | |
| 6,428,542 B1 | 8/2002 | Michelson | |
| 6,432,106 B1 | 8/2002 | Fraser | |
| 6,454,769 B2 | 9/2002 | Wagner et al. | |
| 6,454,771 B1 | 9/2002 | Michelson | |
| 6,485,517 B1 | 11/2002 | Michelson | |
| 6,503,250 B2 | 1/2003 | Paul | |
| 6,527,776 B1 | 3/2003 | Michelson | |
| 6,533,786 B1 | 3/2003 | Needham et al. | |
| 6,558,423 B1 | 5/2003 | Michelson | |
| 6,558,424 B2 | 5/2003 | Thalgott | |
| 6,569,201 B2 | 5/2003 | Moumene et al. | |
| 6,575,975 B2 | 6/2003 | Brace et al. | |
| 6,592,586 B1 | 7/2003 | Michelson | |
| 6,599,290 B2 | 7/2003 | Bailey et al. | |
| 6,602,256 B1 | 8/2003 | Hayes | |
| 6,602,257 B1 | 8/2003 | Thramann | |
| 6,605,090 B1 | 8/2003 | Trieu et al. | |
| 6,613,053 B1 | 9/2003 | Collins et al. | |
| 6,616,666 B1 | 9/2003 | Michelson | |
| 6,620,163 B1 | 9/2003 | Michelson | |
| 6,626,907 B2 | 9/2003 | Campbell et al. | |
| 6,652,525 B1 | 11/2003 | Assaker et al. | |
| 6,669,700 B1 | 12/2003 | Farris et al. | |
| 6,676,703 B2 | 1/2004 | Biscup | |
| 6,679,883 B2 | 1/2004 | Hawkes et al. | |
| 6,699,249 B2 | 3/2004 | Schlapfer et al. | |
| 6,712,818 B1 | 3/2004 | Michelson | |
| 6,755,833 B1 | 6/2004 | Paul et al. | |
| 6,776,798 B2 | 8/2004 | Camino et al. | |
| 6,837,905 B1 | 1/2005 | Lieberman | |
| 6,890,334 B2 | 5/2005 | Brace et al. | |
| 6,916,320 B2 | 7/2005 | Michelson | |
| 6,926,737 B2 | 8/2005 | Jackson | |
| 6,936,050 B2 | 8/2005 | Michelson | |
| 6,936,051 B2 | 8/2005 | Michelson | |
| 6,964,664 B2 | 11/2005 | Freid et al. | |
| 6,969,390 B2 | 11/2005 | Michelson | |
| 7,001,387 B2 | 2/2006 | Farris et al. | |
| 7,033,394 B2 | 4/2006 | Michelson | |
| 7,041,105 B2 | 5/2006 | Michelson | |
| 7,041,135 B2 | 5/2006 | Michelson | |
| 7,044,952 B2 | 5/2006 | Michelson | |
| 7,048,739 B2 | 5/2006 | Konieczynski et al. | |
| 7,060,097 B2 | 6/2006 | Fraser et al. | |
| 7,074,221 B2 | 7/2006 | Michelson | |
| 7,077,843 B2 | 7/2006 | Thramann et al. | |
| 7,097,645 B2 | 8/2006 | Michelson | |
| 7,112,202 B2 | 9/2006 | Michelson | |
| 7,112,222 B2 | 9/2006 | Fraser et al. | |
| 7,115,130 B2 | 10/2006 | Michelson | |
| 7,118,573 B2 | 10/2006 | Michelson | |
| 7,137,984 B2 | 11/2006 | Michelson | |
| 7,186,256 B2 | 3/2007 | Michelson | |
| 7,201,753 B2 | 4/2007 | Schlapfer et al. | |
| 7,229,477 B2 | 6/2007 | Biscup | |
| 7,255,699 B2 | 8/2007 | Paul | |
| 7,273,481 B2 | 9/2007 | Lombardo et al. | |
| 7,303,564 B2 | 12/2007 | Freid et al. | |
| 7,399,301 B2 | 7/2008 | Michelson | |
| 7,611,527 B2 | 11/2009 | Freid et al. | |
| 7,637,951 B2 | 12/2009 | Michelson | |
| 7,637,954 B2 | 12/2009 | Michelson | |
| 7,651,517 B2 | 1/2010 | Konieczynski et al. | |
| 7,955,362 B2 | 6/2011 | Erickson et al. | |
| 2002/0045898 A1 | 4/2002 | Freid et al. | |
| 2002/0058939 A1 | 5/2002 | Wagner et al. | |
| 2002/0120273 A1 | 8/2002 | Needham et al. | |
| 2002/0143400 A1 | 10/2002 | Biscup | |
| 2002/0173790 A1 | 11/2002 | Chang et al. | |
| 2002/0183755 A1 | 12/2002 | Michelson | |
| 2002/0183756 A1 | 12/2002 | Michelson | |
| 2002/0183757 A1 | 12/2002 | Michelson | |
| 2002/0188296 A1 | 12/2002 | Michelson | |
| 2003/0018335 A1 | 1/2003 | Michelson | |
| 2003/0023307 A1 | 1/2003 | Michelson | |
| 2003/0045880 A1 | 3/2003 | Michelson | |
| 2003/0060828 A1 | 3/2003 | Michelson | |
| 2003/0078668 A1 | 4/2003 | Michelson | |
| 2003/0105462 A1* | 6/2003 | Haider | 606/69 |
| 2003/0181912 A1 | 9/2003 | Michelson | |
| 2003/0187443 A1 | 10/2003 | Lauryssen et al. | |
| 2003/0191471 A1 | 10/2003 | Michelson | |
| 2003/0191472 A1 | 10/2003 | Michelson | |
| 2003/0199876 A1 | 10/2003 | Brace et al. | |
| 2003/0199983 A1 | 10/2003 | Michelson | |
| 2003/0208204 A1 | 11/2003 | Bailey et al. | |
| 2003/0225409 A1 | 12/2003 | Freid et al. | |
| 2004/0019353 A1 | 1/2004 | Freid et al. | |
| 2004/0030338 A1 | 2/2004 | Paul | |
| 2004/0092939 A1 | 5/2004 | Freid et al. | |

(56) References Cited

U.S. PATENT DOCUMENTS

| | | |
|---|---|---|
| 2004/0097934 A1 | 5/2004 | Farris et al. |
| 2004/0122426 A1 | 6/2004 | Michelson |
| 2004/0127896 A1 | 7/2004 | Lombardo et al. |
| 2004/0127897 A1 | 7/2004 | Freid et al. |
| 2004/0127903 A1 | 7/2004 | Schlapfer et al. |
| 2004/0127904 A1 | 7/2004 | Konieczynski et al. |
| 2004/0133205 A1 | 7/2004 | Thramann et al. |
| 2004/0181226 A1 | 9/2004 | Michelson |
| 2004/0181229 A1 | 9/2004 | Michelson |
| 2004/0186476 A1 | 9/2004 | Michelson |
| 2004/0193269 A1 | 9/2004 | Fraser et al. |
| 2004/0193270 A1 | 9/2004 | DiMauro et al. |
| 2004/0193271 A1 | 9/2004 | Fraser et al. |
| 2004/0210313 A1 | 10/2004 | Michelson |
| 2004/0230309 A1 | 11/2004 | DiMauro et al. |
| 2005/0038513 A1 | 2/2005 | Michelson |
| 2005/0096657 A1* | 5/2005 | Autericque et al. ............ 606/69 |
| 2006/0241616 A1 | 10/2006 | Konieczynski et al. |
| 2007/0073297 A1 | 3/2007 | Reynolds |
| 2008/0097444 A1* | 4/2008 | Erickson et al. ................ 606/69 |

FOREIGN PATENT DOCUMENTS

| | | |
|---|---|---|
| CA | 2163243 | 9/1995 |
| CA | 2383634 | 8/2001 |
| DE | 4409833 | 10/1995 |
| EP | 0179695 | 4/1986 |
| EP | 0307241 | 3/1989 |
| EP | 1437105 | 7/2004 |
| GB | 0401362.9 | 2/2004 |
| WO | 8909035 | 10/1989 |
| WO | 9720526 | 6/1997 |
| WO | 9963914 | 12/1999 |
| WO | 0066044 | 11/2000 |
| WO | 0066045 | 11/2000 |
| WO | 2007035582 | 3/2007 |
| WO | 2008021656 | 2/2008 |

* cited by examiner

IMPLANT PLATE SCREW LOCKING SYSTEM AND SCREW HAVING A LOCKING MEMBER

RELATED APPLICATIONS

This application is a continuation of U.S. patent application Ser. No. 11/778,284, filed Jul. 6, 2007, which is incorporated herein by reference and made a part hereof.

BACKGROUND OF THE INVENTION

1. Field of the Invention

This invention relates to a implant plate system, device and locking screw having at least one locking member. The preferred application for the device is in spinal surgery, however, applications in other areas of orthopedic surgery are appropriate.

2. Description of the Related Art

Many types of prosthetic devices have been proposed in the past. For example, U.S. Pat. No. 5,192,327 to Brantigan concerns a surgical prosthetic modular implant used singularly or stacked together to support and fuse together adjacent vertebrae or to totally or partially replace one or more vertebrae in a vertebral column. Other surgical implant devices and methods are shown in U.S. Pat. Nos. 4,488,543; 5,192,327; 5,261,911; 5,549,612; 5,713,899; 5,776,196; 6,136,002; 6,159,245; 6,224,602; 6,258,089; 6,261,586; 6,264,655; 6,306,136; 6,328,738; 6,361,537 and 6,592,586. Some or all of these devices have improved the success rate and have simplified the surgical techniques in inter-body veritable fusion.

U.S. Pat. No. 6,258,089 B1 issued Jul. 10, 2001 to Campbell et al. for an Anterior Cervical Plate And Fixation System discloses an anterior cervical plate is disclosed, along with threaded fasteners for securing the plate to vertebrae or other osseous material. The cervical plate has several pockets or apertures, preferably at least four, to receive a corresponding number of the fasteners. The pockets have spherical surfaces, and the fasteners have heads with similarly sized spherical surfaces, which when engaged permit each of the fasteners to be oriented at a variety of projection angles with respect to the plate. In connection with each pocket, the cervical plate incorporates a fastener retaining feature. The feature can take the form of a cantilevered tab or a beam supported at its opposite ends, in each case plastically deformable between an open position for admitting the fastener and a closed position for preventing retraction.

U.S. Pat. No. 5,549,612 issued Aug. 27, 1996 to Yapp et al. for Osteosynthesis Plate System discloses an osteosynthesis plate system is particularly well adapted to securely fuse adjacent cervical vertebrae. The plates are adapted for mounting upon the anterior or posterior surfaces of the vertebrae. Plates for mounting on the anterior vertebral surfaces have a concave bone contacting surface and a bone screw locking mechanism integral with each screw hole. Moreover, the bone contacting surface of the plate has a plurality of bone penetrating protrusions to more securely affix the plate to bone. Plates for mounting on the posterior vertebral surfaces also have bone penetrating protections on their bone contacting surfaces. Such plates are formed so as to have a curved bone contacting surface that is concave in the transverse axis of the plate and convex in the longitudinal axis of the plate. The screw holes of such plates are constructed so as to guide a bone screw along a desired angle to improve the anchoring of the screws in bone.

U.S. Pat. No. 4,488,543 issued Dec. 18, 1984 to Tornier for Device For Osteosynthesis Of Fractures Of The Extremities Of The Femur discloses a device for osteosynthesis of the fractures of the extremities of the femur comprises a plate in which holes are provided for the passage of screws intended to be inserted into the bone to make the fractured bone and the plate solid. One end of the plate to be applied against one of extremities of the femur is wider than the other end and includes three holes arranged in an isosceles triangle. The median plane of the one end defines a plane which forms, with the plane of the rest of the plate, an obtuse angle of between 160° and 175°.

U.S. Pat. No. 6,361,537 B1 issued Mar. 26, 2002 to Anderson for Surgical Plate With Pawl And Process For Repair Of A Broken Bone discloses a surgical plate and process for preventing screw backout of repaired bones. At least one pawl is provided on a surgical plate adjacent to a screw hole. A screw having a ratchet wheel is inserted through the hole and screwed into the bone. The pawl engages the ratchet wheel to prevent rotational movement of the screw to prevent the screw from backing out. In a preferred embodiment, a pawl plate comprising a base portion is rigidly connected to the surgical plate and a torsion bar is pivotally connected to the base portion. The pawl is positioned at the end of the torsion bar. In the preferred embodiments, several of these special screw holes with pawls, and several screws (each with a ratchet wheel) are used in bone repair.

While the above approaches may have yielded favorable results in certain circumstances, there remains a need for reducing the need for multiple parts or tools and for providing a simpler, more reliable means and system of facilitating prevention of the screws from migrating out of the bone by axial or rotational movement after the plate is fixed thereto.

Among some of the problems associated with the prior art devices is that after the device is inserted into a patient during a surgical procedure, there was a possibility of inadequate fixation of the implant device due to false-locking of fixating screws.

Another problem with the prior art devices is that the implant device and associated bone graft could loosen after the surgical procedure due to undesired back-out of fixating screws.

Moreover, in some of the prior art devices, the fixation screws are locked to the prosthetic device in a multiple-step process, increasing the possibility for user error or false fixation.

Another problem with prior art implant plate systems is that the screws or fasteners which secured the plate had a tendency to withdraw, causing injury to local structures by the screws themselves.

What is needed, therefore, is a system and method, which facilitates overcoming one or more of the aforementioned problems as well as other problems and to provide a device that has unique features that will facilitate reducing the risk associated with neurological surgeries and advance the present state of the art.

Therefore, there is a need for a plate and fixation system in which bone screws or other fasteners are more securely retained and less likely to work loose or migrate, which reduces or eliminates the need for auxiliary components, screws, tools or additional fixtures.

SUMMARY OF THE INVENTION

It is, therefore, one object of the embodiments to provide a plate having an improved locking system which in one illustrative embodiment comprises a screw having a member, such as a resilient pawl, that is received in a channel in the plate to facilitate preventing screw migration.

In one aspect this invention comprises a plate system comprising a screw having a screw head, a plate having an aperture for receiving the screw, and the screw comprising at least one pawl for restricting or preventing the screw from moving in at least one of an axial direction or a rotational direction.

In another aspect this invention comprises a locking screw for use in a plate, comprising a threaded portion, a screw head, and the screw head comprising at least one member for cooperating with the plate to prevent migration or movement of the screw head.

These and other objects and advantages of the invention will be apparent from the following description, the accompanying drawings and the appended claims.

DETAILED DESCRIPTION OF PREFERRED EMBODIMENTS

Figures 1, 3, 5:
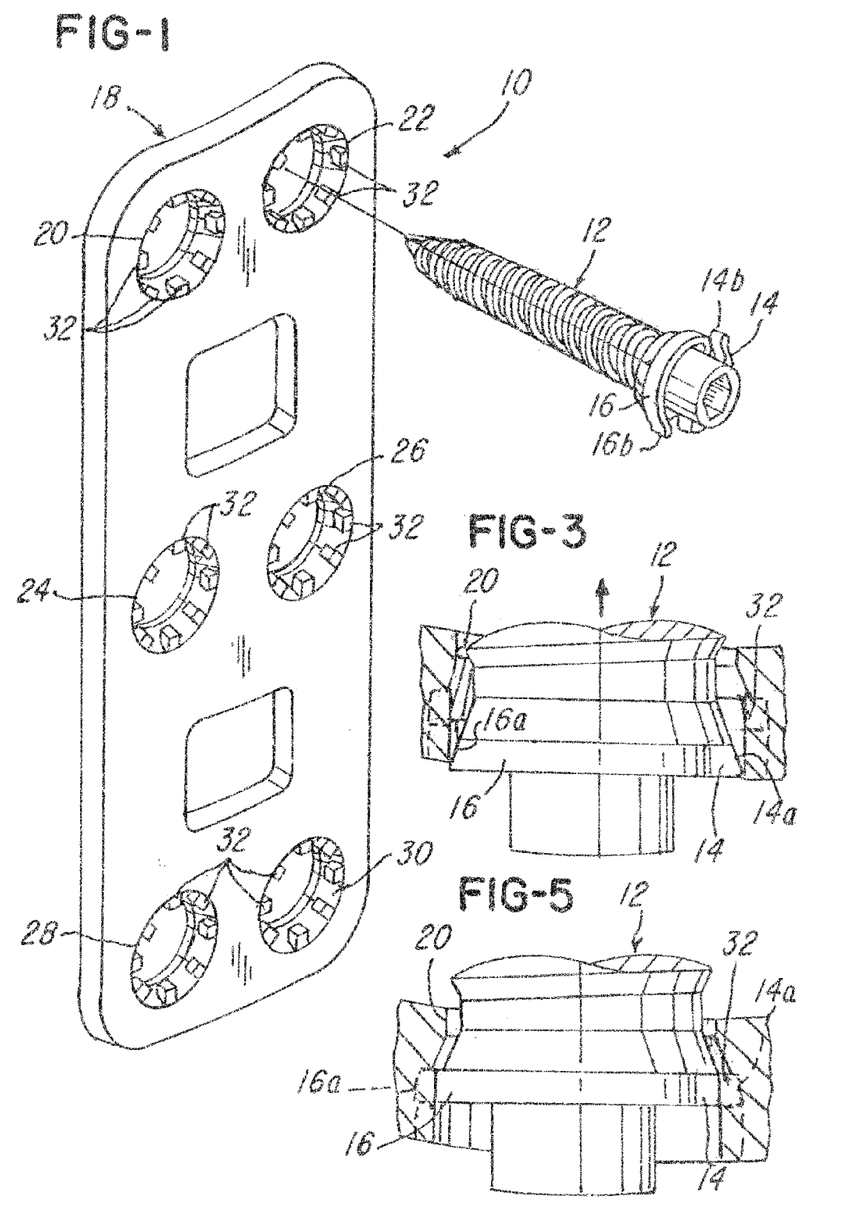
FIG. 1 is a perspective view illustrating one embodiment of the invention where at least one or a plurality of pawls are embodied in the screw.
FIGS. 2-5 are various fragmentary views illustrating various details of the embodiment shown in FIG. 1.
Figure 2:
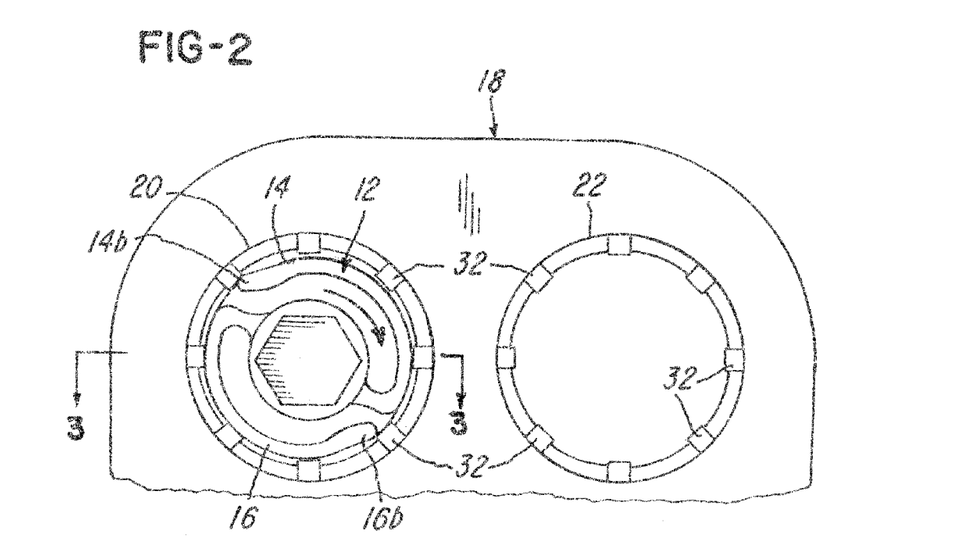

Referring now to FIGS. 1-17, means and apparatus for preventing axial and/or rotational movement in the form of a resilient lock may be provided. FIGS. 1-17 illustrate a system and method for providing an integral lock. In FIG. 1, a system 10 comprises a screw 12 comprises at least one or a plurality of resilient fingers, springs, pawls, elastic projections or members 14 and 16. The fingers or members are resilient, elastic and deflectable as with prior embodiments. In the illustration being described, the fingers or members 14 and 16 are integrally formed in the screw 12, but they could be non-integral or assembled from multiple parts.

Notice in the embodiment illustrated in FIGS. 1-5 that a plate 18 is provided having a plurality of apertures 20, 22, 24, 26, 28 and 30. In this embodiment, the plate 18 comprises a plurality of notches, projections or stops 32 associated with each aperture. The members 14 and 16 are normally biased a predetermined distance away from the axis of the screw 12 so that when the screw 12 is received in an aperture, such as aperture 20, the screw 12 becomes locked or retained in the plate 18.

Figure 4:
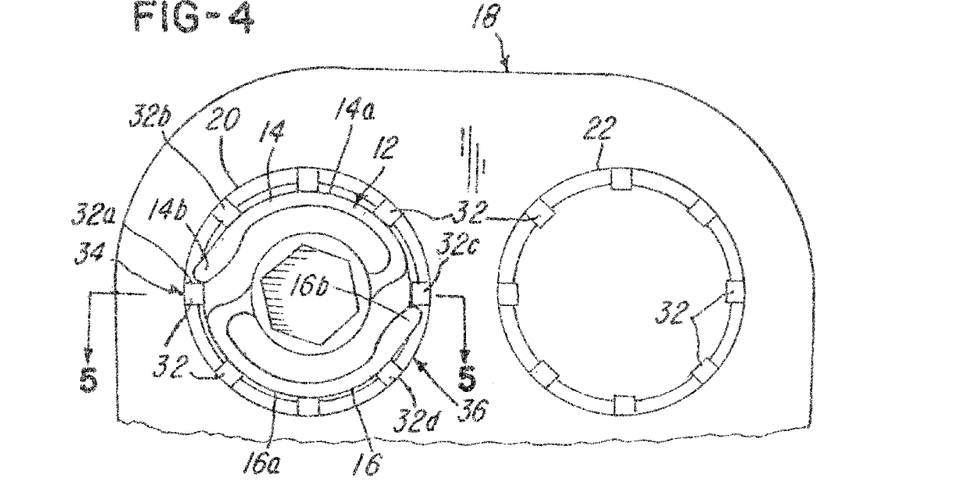
Figure 6:
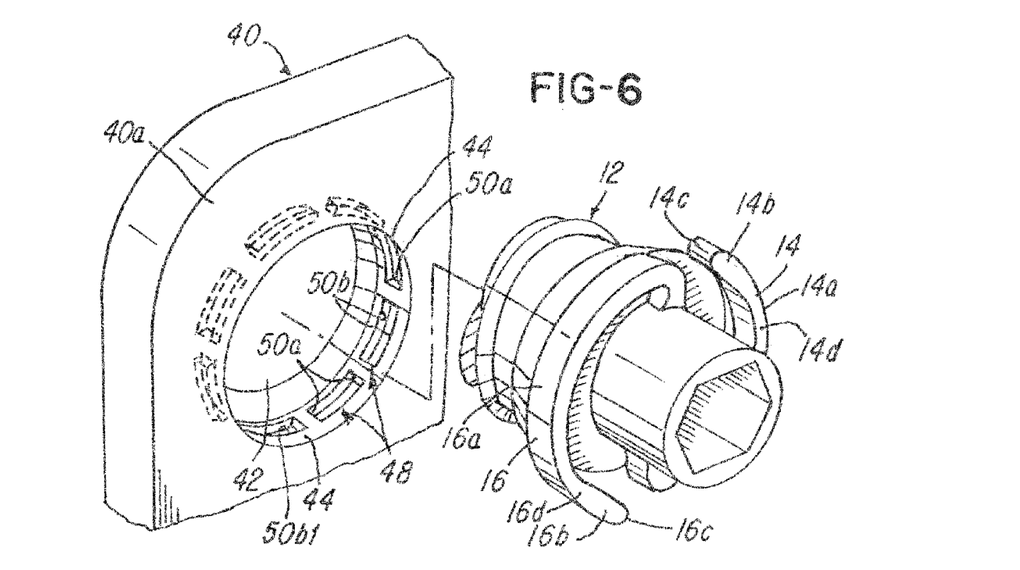
FIG. 6 is a perspective and fragmentary view of another embodiment of the invention showing various notched-out areas in the plate.
Figure 7:
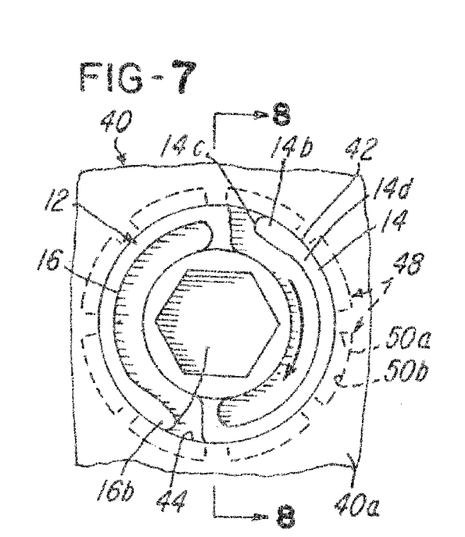
FIGS. 7-10 are various fragmentary and sectional views showing various details of the embodiment shown in FIG. 6.

Notice in FIG. 3 that the pawls 14 and 16 comprise beveled, curved or angled surfaces 14a and 16a which engage the notches 32a, 32b and 32c, 32d, respectively, and deflected inwardly (as viewed in FIG. 2) toward an axis of the screw 12 as the screw 12 is screwed into bone. After the screw 12 is screwed into the bone to a desired depth, an end 14b (FIG. 1) of finger 14 and an end 16b of finger 16 becomes received between adjacent notches 32, such as in areas 34 and 36 (FIG. 4), between adjacent notches 32. Notice that a surface 32a (FIG. 4) of at least one notch 32 engages end 14b of the resilient pawl 14, which prevents rotational movement in a counterclockwise direction (as viewed in FIG. 4). At this point, ends 14b and 16b of fingers or pawls 14 and 16, respectively, are received in the areas 34 and 36 as illustrated in FIG. 4.

Thus, in the embodiment being illustrated, FIGS. 1-5, the pawls 14 and 16 cooperate with the notches or projections 32 to prevent rotational movement of the screw 12 after it is received in the plate 18 and in the bone.

FIGS. 6-10 and 16 illustrate another embodiment wherein both axial and rotational movement of the screw 12 is prevented or restricted. In this embodiment, a plate 40, which is shown only in fragmentary view for ease of illustration and description, is provided with at least one or a plurality of screw-receiving apertures 42, as best described in FIG. 6. In this regard, the plate 40 comprises a wall 44 defining the screw-receiving aperture 42. The wall 44 also comprises a plurality of notched-out areas 48 associated with aperture 42. Each of the plurality of notched-out areas 48 is defined by a wall 50 having side or wall surfaces 50a and inner surfaces 50b that cooperate to define the notched out area 48.

Figure 8:
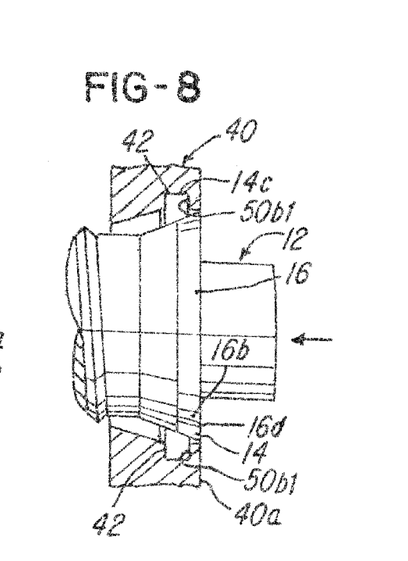
Figure 9:
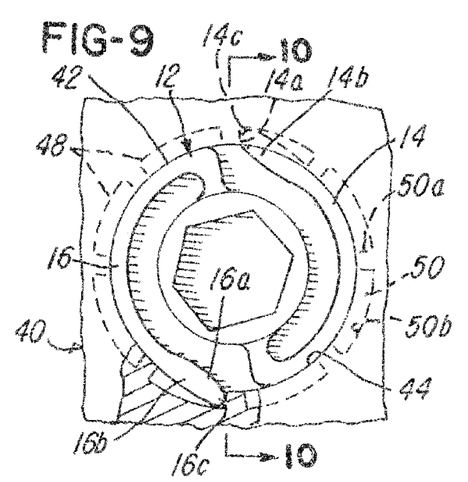
Figure 10:
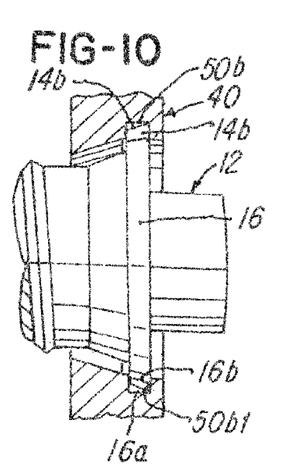

As illustrated in FIGS. 8 and 10, the pawls or fingers 14 and 16 may comprise beveled or angled camming surfaces 14a and 16a, respectively, that resiliently deflect inwardly toward the axis of screw 12 after the screw 12 is received in the aperture defined by wall 52 and screwed into the bone. In the embodiment illustrated in FIGS. 6-10, the surfaces 14a and 16a engage the surface or edge 44 (FIG. 6) of the plate 40 and yield inwardly (as viewed in FIGS. 7-8) toward the axis of the screw 12. After the surface 14b of pawl 14 and surface 16b of pawl 16 clear the surface 50b1 (FIG. 8), the ends 14c and 16c of resilient pawls 14 and 16 move outwardly or away from the axis of the screw 12 until at least a portion, such as ends 14c and 16c, are received in one of the notched-out areas 48, whereupon the surfaces 14d and 16d (FIG. 6) become operatively related to and generally opposed to the surface 50b1, as illustrated in FIGS. 9-10.

Notice that when the pawls 14 and 16 are in the locked position, the screw 12 is prevented or restricted from moving, migrating or withdrawing axially (i.e., to the right as viewed in FIG. 10). Notice also that the walls 50a of notched-out areas 48 cooperate with ends 14c and 16c to restrict or prevent rotational movement of the screw 12 in a counter-clockwise direction in the illustration being described.

Figure 12:
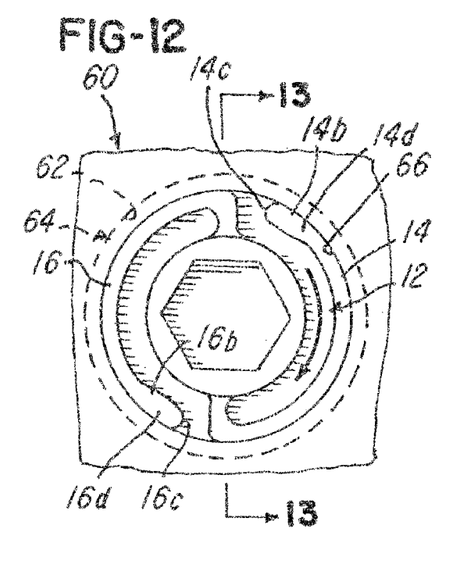
FIGS. 12-15 are various fragmentary and sectional views illustrating various details of the embodiments shown in FIG. 11.
Figure 13:
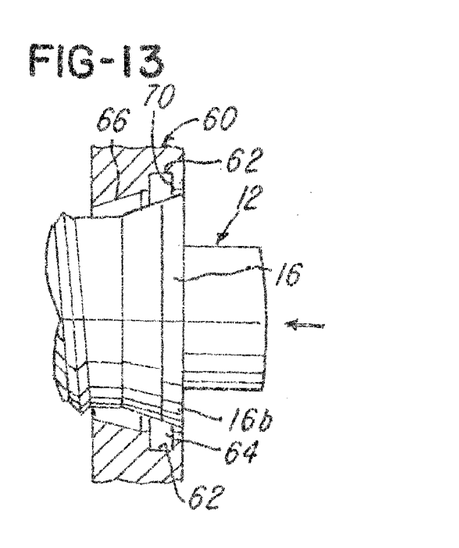
Figure 14:
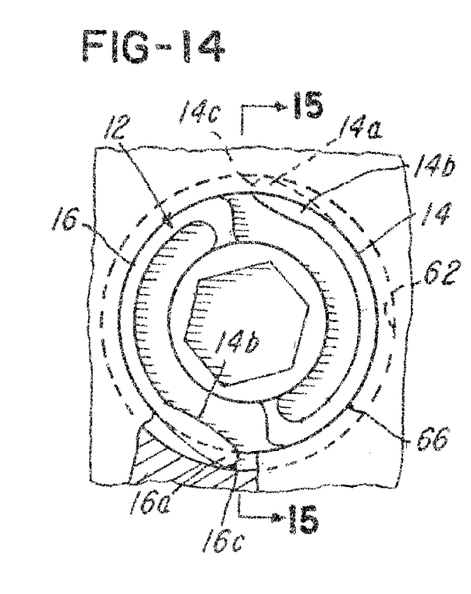
Figure 15:
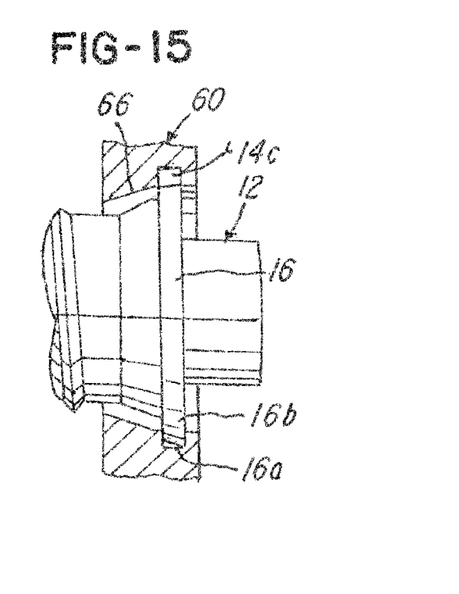

FIGS. 11-15 and 17 show a similar arrangement except that a plate 60 comprises a U-shaped wall or surface 62 that defines a single, continuous notched-out area, endless channel, or channel 64. In this embodiment, at least a portion of the ends 14c and 16c are received in the channel or notched-out area 64, as shown in FIGS. 14-15. As with the embodiment described relative to FIGS. 6-10 and 16, this embodiment also prevents axial movement of the screw 12.

Figure 11:
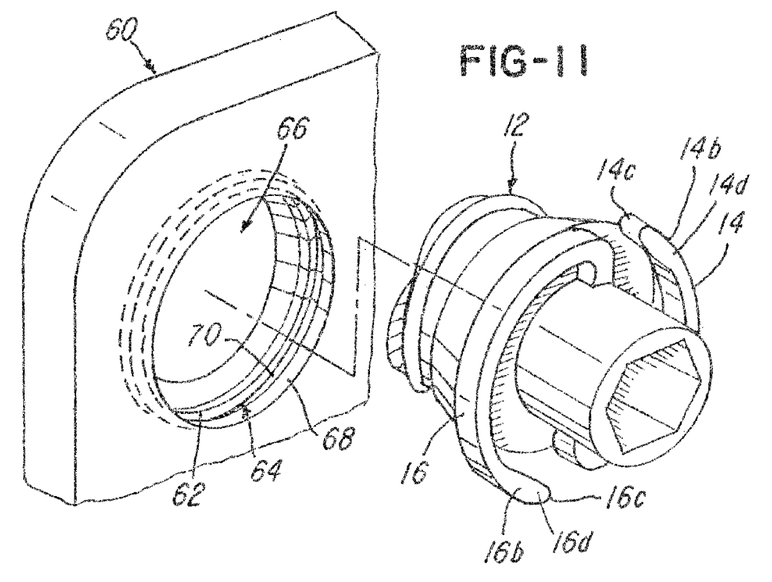
FIG. 11 is a fragmentary perspective view illustrating another embodiment of the invention with a continuous channel in a plate.

After screw 12 is received in an aperture, such as aperture 66 (FIG. 11) of plate 60, as best seen in FIG. 11, the angled surfaces 14a and 16a engage or cam against the surface 68 (FIG. 11) and are deflected inwardly, as illustrated in FIGS. 12-13. The screw 12 is driven until the surfaces 14a and 16a clear the wall or surface 70 (FIG. 11), whereupon at least a portion of the fingers, such as ends 14c and 16c, spring or move away from the screw axis end and are received in the channel 64, whereupon the surfaces 14d (FIG. 12) and 16d become generally opposed to surface 70 (FIG. 13). This prevents or restricts axial movement or withdrawal of the screw 12 from the bone and plate 60.

Figure 16:
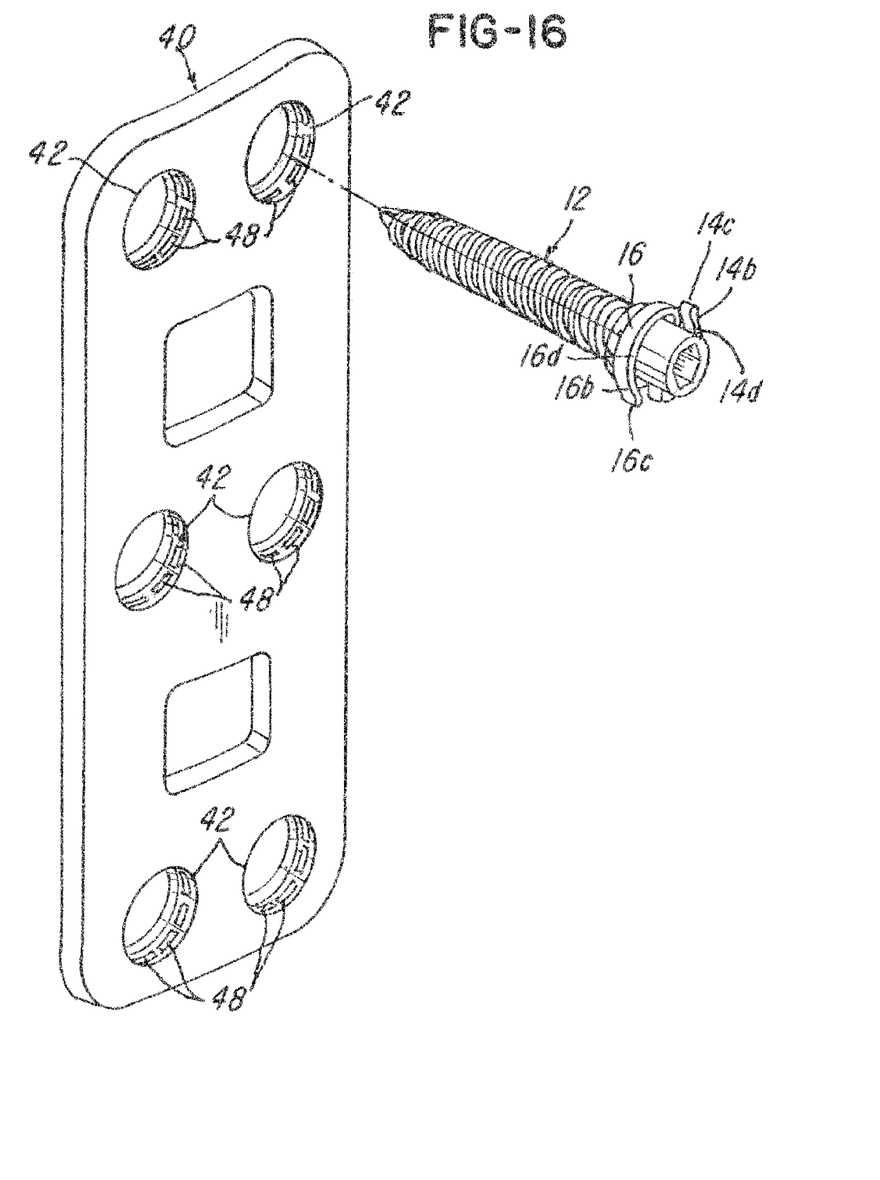
FIG. 16 is a perspective view showing the screw and plate according to the embodiment illustrated in FIGS. 6-10.
Figure 17:
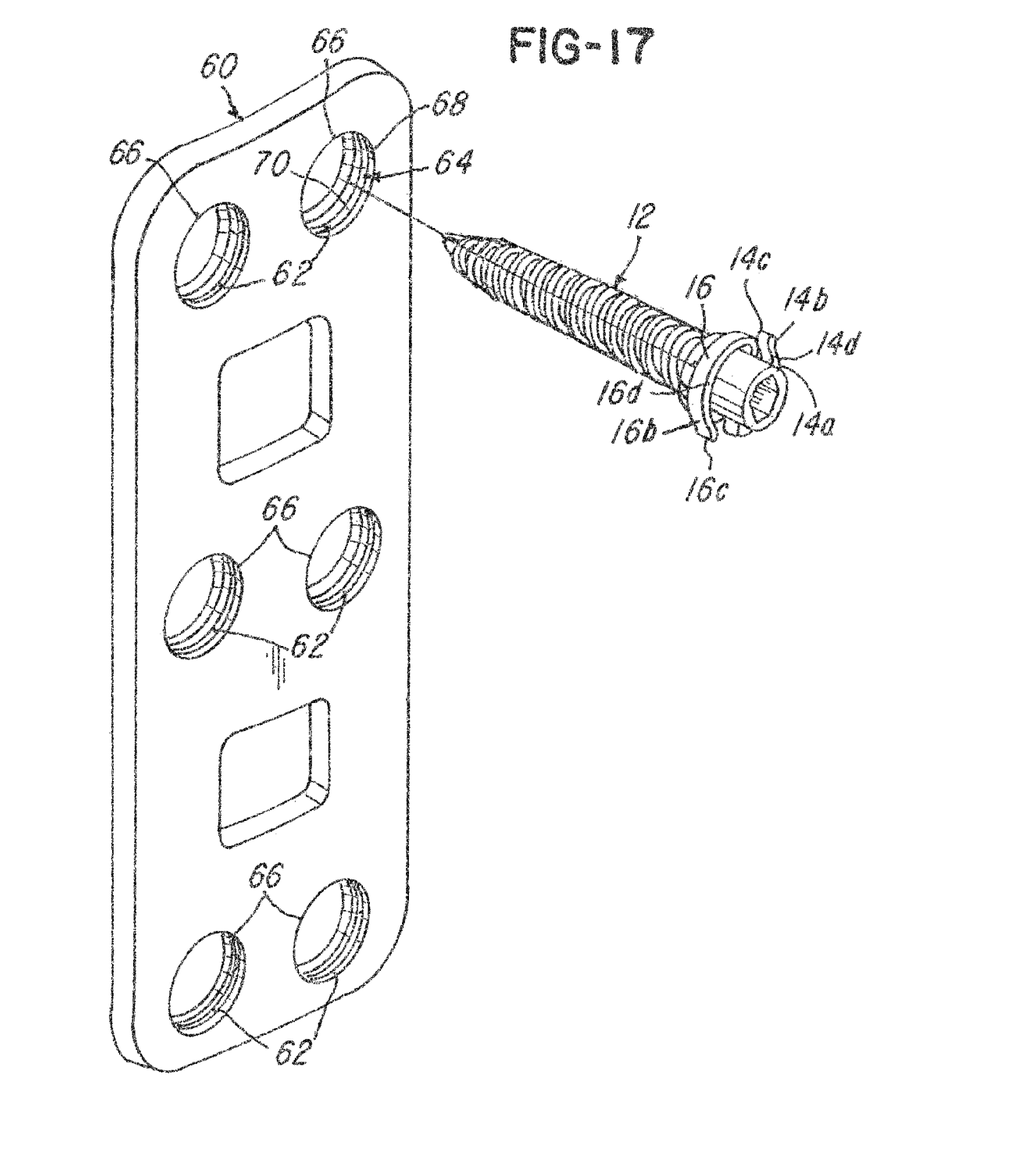
FIG. 17 is a perspective view of the embodiment corresponding to the embodiments shown in FIGS. 11-15.

FIGS. 16 and 17 are perspective views of the entire plate and screws for the embodiments shown in FIGS. 6-10 and 11-15, respectively. Of course, the various pawls, fingers, notched-out areas, notches and the like described could be adapted to have other shapes or configurations, with more or fewer of them, for example, without departing from the desire to provide a locking system and method that provides means for restricting axial and rotational movement of a screw in a plate.

Advantageously, various embodiments described relative to FIGS. 1-17 provide various means, apparatus and methods for preventing axial and/or rotational movement of the screw and for providing an integral lock to facilitate retaining the screw in a bone, such as a spinal bone. The system and method according to these embodiments show various means for providing a lock for retaining the screw in the plate in which it is received.

Advantageously, the system and method provide means and apparatus for locking a screw to a plate and preventing withdrawal of the screw or unscrewing of the screw. The illustrative embodiments provide means and apparatus for facilitating preventing rotational movement of at least one or a plurality of screws in at least one or a plurality of directions and axial movement of the at least one or a plurality of screws.

While the apparatus and method described constitute preferred embodiments of this invention, it is to be understood that the invention is not limited to this precise apparatus and method, and that changes may be made in either without departing from the scope of the invention, which is defined in the appended claims.

What is claimed is:

1. A plate system for implanting into a patient comprising:
a screw having a screw head, said screw being adapted to be screwed into bone of the patient;
a plate having at least one wall that defines at least one aperture for receiving said screw; and
said screw head comprising at least one member for restricting or preventing said screw from moving in an axial direction;
wherein said at least one member is an elastic or resilient pawl having one end that is integral with said screw head;
said plate further comprising a continuous and endless channel in communication with said at least one wall for receiving at least a portion of said at least one member and for restricting or preventing said screw from moving in said axial direction, said continuous and endless channel being at least partially defined by an interior wall that is below a top surface of said plate, said elastic or resilient pawl having an upper most pawl surface, at least a portion of which becomes generally opposed to and situated below said interior wall after said at least a portion of said elastic or resilient pawl is received in said continuous and endless channel, thereby facilitating preventing said screw from withdrawing from said plate, each of said upper most pawl surfaces and said interior wall lying between a top surface and bottom surface of said plate.

2. The plate system as recited in claim 1 wherein said at least one member comprises a plurality of pawls and said plate being adapted to define at least one notched-out area or receiving area for receiving at least a portion of each of said plurality of pawls.

3. The plate system as recited in claim 1 wherein said plate comprises a plurality of walls that define a plurality of screw-receiving apertures for receiving a plurality of screws, respectively, each of said plurality of screws having said at least one member integrally formed on said screw head.

4. The plate system as recited in claim 1 wherein said at least one member comprises a plurality of pawls.

5. The plate system as recited in claim 4 wherein said plurality of pawls are integral with said screw head.

6. The plate system as recited in claim 4 wherein each of said plurality of pawls are resilient or elastic.

7. The plate system as recited in claim 1 wherein said screw comprises a plurality of pawls that are generally curved or arcuate.

8. The plate system as recited in claim 7 wherein said plurality of pawls are resilient or elastic, each of said plurality of pawls comprising an end that is normally biased away from an axis of said screw.

9. The plate system as recited in claim 1 wherein said plate comprises a plurality of apertures defined by a plurality of surfaces, said plurality of surfaces defining at least one channel for receiving said at least one member, thereby preventing said screw from moving in said axial direction.

10. A locking screw system for use with an implant plate for implanting into a patient, comprising:
a threaded portion;
a screw head, said screw head being adapted to be screwed into bone of the patient; and
said screw head comprising at least one member for cooperating with said plate to facilitate preventing migration or movement of said screw head;
wherein at least one member is an elastic or resilient pawl having one end that is integral with said screw head;
said plate further comprising a continuous and endless channel in communication with said at least one wall for receiving at least a portion of said at least one member and for restricting or preventing said screw from moving in said axial direction, said continuous and endless channel being at least partially defined by an interior wall that is below a top surface of said plate, said elastic or resilient pawl having an upper most pawl surface, at least a portion of which becomes generally opposed to and situated below said interior wall after said at least a portion of said elastic or resilient pawl is received in said continuous and endless channel, thereby facilitating preventing said screw from withdrawing from said plate, each of said upper most pawl surfaces and said interior wall lying between a top surface and bottom surface of said plate.

11. The locking screw system as recited in claim 10 wherein said at least one member is a resilient pawl.

12. The locking screw system as recited in claim 11 wherein said resilient pawl is integral with said screw head.

13. The locking screw system as recited in claim 12 wherein said resilient pawl is arcuate or curved.

14. The locking screw system as recited in claim 10 wherein said at least one member has an end and a curved portion joining said end to said screw, said at least one member being resilient and causing said end to be normally biased away from an axis of said screw a predetermined distance so that when said screw is received in said plate, said screw migration or movement is prevented.

15. The locking screw system as recited in claim 10 wherein said screw head comprises a plurality of resilient pawls.

16. The locking screw system as recited in claim 10 wherein said migration or movement is at least one of axial movement or rotational movement of said threaded portion.

17. The locking screw system as recited in claim 10 wherein said migration or movement is axial movement.

* * * * *

UNITED STATES PATENT AND TRADEMARK OFFICE
CERTIFICATE OF CORRECTION

PATENT NO.        : 8,728,130 B2
APPLICATION NO.   : 13/155726
DATED             : May 20, 2014
INVENTOR(S)       : Kirschman Page 1 of 1

It is certified that error appears in the above-identified patent and that said Letters Patent is hereby corrected as shown below:

Claims

Claim 10, Column 6, line 31, after "wherein" insert -- said --.

Claim 10, Column 6, line 37, delete "in said" and insert -- in an -- therefor.

Signed and Sealed this
Eighth Day of December, 2015

Michelle K. Lee
*Director of the United States Patent and Trademark Office*